United States Patent
Laudanski et al.

(10) Patent No.: US 10,682,513 B2
(45) Date of Patent: **\*Jun. 16, 2020**

(54) HEARING ASSISTANCE DEVICE COMPRISING AN IMPLANTED PART FOR MEASURING AND PROCESSING ELECTRICALLY EVOKED NERVE RESPONSES

(71) Applicant: Oticon Medical A/S, Smørum (DK)

(72) Inventors: Jonathan Laudanski, Vallauris (FR); Nicolas Veau, Vallauris (FR)

(73) Assignee: OTICON MEDICAL A/S, Smorum (DK)

(*) Notice: Subject to any disclaimer, the term of this patent is extended or adjusted under 35 U.S.C. 154(b) by 0 days.

This patent is subject to a terminal disclaimer.

(21) Appl. No.: 16/045,464

(22) Filed: Jul. 25, 2018

(65) Prior Publication Data

US 2019/0070412 A1    Mar. 7, 2019

Related U.S. Application Data

(62) Division of application No. 14/330,572, filed on Jul. 14, 2014, now Pat. No. 10,099,054.

(30) Foreign Application Priority Data

Jul. 15, 2013  (EP) .................................. 13176510

(51) Int. Cl.
*A61N 1/36* (2006.01)
*A61N 1/02* (2006.01)
(Continued)

(52) U.S. Cl.
CPC ......... *A61N 1/36036* (2017.08); *A61N 1/025* (2013.01); *A61N 1/36039* (2017.08); *A61B 5/04001* (2013.01); *A61N 1/0541* (2013.01)

(58) Field of Classification Search
CPC .............. A61N 1/0541; A61N 1/36036; A61N 1/36038; A61N 1/36039
See application file for complete search history.

(56) References Cited

U.S. PATENT DOCUMENTS

4,207,441 A   6/1980  Ricard et al.
4,532,930 A   8/1985  Crosby et al.
(Continued)

FOREIGN PATENT DOCUMENTS

CN    102215796 A    10/2011
CN    103656855 A     3/2014
WO    WO 2010/045358 A1    4/2010

OTHER PUBLICATIONS

Botros, Andrew et al. AutoNRT: An automated system that measures ECAP thresholds with the Nucleus Freedom cochlear implant via machine intelligence. Artificial Intelligence in Medicine (2007) 40, 15-28. (Year: 2007).*

(Continued)

*Primary Examiner* — Allen Porter
(74) *Attorney, Agent, or Firm* — Birch, Stewart, Kolasch & Birch, LLP

(57) ABSTRACT

The application relates to a hearing assistance device comprising an implanted part and to a method of its operation. The disclosure aims at improving the identification and processing of recorded nerve response data in an implanted part. The implanted part comprises a) A multitude of electrodes; b) Stimulation circuitry electrically coupled to a stimulation electrode during a stimulation time period; c) Measurement circuitry electrically coupled to a recording electrode during a measurement time period; d) A control unit configured to control the timing of the application of the stimulation signal in the stimulation time period and to control the measurement time period relative to the stimulation time period; and e) A processing unit configured to (Continued)

record the measured signal in the measurement time period and to identify a response from the auditory nerve based on said measured signal. The invention may e.g. be used for cochlear implant type hearing aids.

14 Claims, 7 Drawing Sheets

(51) Int. Cl.
*A61B 5/04* (2006.01)
*A61N 1/05* (2006.01)

(56) References Cited

U.S. PATENT DOCUMENTS

| | | |
|---|---|---|
| 2004/0010180 A1 | 1/2004 | Scorvo |
| 2005/0101875 A1 | 5/2005 | Semler et al. |
| 2005/0101878 A1 | 5/2005 | Daly et al. |
| 2007/0142733 A1 | 6/2007 | Hatlestad et al. |
| 2007/0156190 A1 | 7/2007 | Cinbis |
| 2007/0179565 A1 | 8/2007 | Overstreet et al. |
| 2008/0147135 A1 | 6/2008 | Hareland |
| 2008/0249589 A1 | 10/2008 | Cornejo Cruz et al. |
| 2008/0285773 A1 | 11/2008 | Nongpiur et al. |
| 2008/0319505 A1 | 12/2008 | Boyden et al. |
| 2008/0319508 A1 | 12/2008 | Botros et al. |
| 2009/0112051 A1 | 4/2009 | Miller, III |
| 2009/0254149 A1 | 10/2009 | Polak |
| 2010/0310084 A1 | 12/2010 | Hersbach |
| 2011/0196247 A1 | 8/2011 | Cao et al. |
| 2012/0011183 A1 | 1/2012 | Nowak et al. |
| 2012/0029377 A1 | 2/2012 | Polak |
| 2012/0116774 A1 | 5/2012 | Forsell |
| 2012/0226331 A1 | 9/2012 | Banna et al. |
| 2012/0253423 A1 | 10/2012 | Youn et al. |

OTHER PUBLICATIONS

Brown et al., "Electrically Evoked Whole-Nerve Action Potentials: Data From Human Cochlear Implant Users", J. Acoust. Soc. Am., Sep. 1990, vol. 88, Issue 3, pp. 1385-1391.

De Sauvage et al., "Acoustically Derived Auditory Nerve Action Potential Evoked by Electrical Stimulation: An Estimation of the Waveform of Single Unit Contribution", . Acoust. Soc. Am., Feb. 1983, vol. 73, Issue 2, pp. 616-627.

Undurraga et al., "Evaluating the Noise in Electrically Evoked Compound Action Potential Measurements in Cochlear Implants", IEEE Transactions on Biomedical Engineering, vol. 59, No. 7, Jul. 2012, pp. 1912-1923.

\* cited by examiner

HEARING ASSISTANCE DEVICE COMPRISING AN IMPLANTED PART FOR MEASURING AND PROCESSING ELECTRICALLY EVOKED NERVE RESPONSES

CROSS-REFERENCE TO RELATED APPLICATIONS

This application is a Divisional of copending application Ser. No. 14/330,572, filed on Jul. 14, 2014, which claims priority under 35 U.S.C. § 119(a) to application Ser. No. 13/176,510.9, filed in Europe on Jul. 15, 2013, all of which are hereby expressly incorporated by reference into the present application.

TECHNICAL FIELD

The present application relates to hearing assistance devices comprising an implanted part, e.g. to a cochlear implant type hearing assistance device. The disclosure relates specifically to a hearing assistance device comprising an implanted part configured to measure and/or process electrically evoked nerve responses (termed 'electrically evoked whole-nerve action potentials' (EAP) by [Brown et al.; 1990], alternatively termed 'electrically evoked auditory potentials' (EAP)), such as electrically evoked compound potentials (eCAPs), or electrically evoked auditory brain stem responses (eABRs).

The application furthermore relates to the use of a hearing assistance device comprising an implanted part and to a method of operating such device.

Embodiments of the disclosure may e.g. be useful in applications such as cochlear implant type hearing aids, in particular during the fitting of such hearing aid to a particular user.

BACKGROUND

Cochlear implant hearing assistance devices have been known in many years in a variety of configurations, but typically comprising a) a number of electrodes implantable in different locations of the cochlea allowing a stimulation of different frequencies of the audible range, b) an external part for picking up and processing sound from the environment, and for determining sequences of pulses for stimulation of the electrodes in dependence on the current input sound, c) a (typically wireless, e.g. inductive) communication link for simultaneously transmitting information about the stimulation sequences and for transferring energy to d) an implanted part allowing the stimulation to be generated and applied to the relevant of said electrodes.

Such systems are e.g. described in U.S. Pat. No. 4,207,441 and in U.S. Pat. No. 4,532,930.

To adapt a cochlear implant type hearing assistance device to a user's particular needs, information about the users' hearing threshold (T) and comfort (C) levels of electrical stimulation intensity as a function of frequency is needed. During a fitting session, electrically evoked compound potentials (eCAPs) in response to various levels of electrical stimulation signals can e.g. be measured for different electrodes stimulating different parts of the auditory nerve. In a subsequent processing procedure, the thus recorded signals can be used to extract the actual electrical nerve responses from the user's nerve cells and by mapping corresponding values of the amplitude of the nerve response signal $A_{eCAP}$ versus the intensity (energy) of the stimulation signal $I_s$, a 'hearing threshold' (T) stimulation intensity $(I_T)$ for each electrode can be determined.

Nerve response measurements (e.g. eCAP-measurements) and their subsequent processing can be performed in a number of different ways, e.g. (in a relatively 'simple' way) by applying electric stimuli to an implanted electrode and using external ABR electrodes (surface pick-up electrodes applied to the skin) to sense the response of the human auditory system. The first human recordings of eCAPs were published by [Brown et al.; 1990] using a method published by [de Sauvage et al.; 1983].

Electrically evoked compound action potentials (eCAPs) are routinely used in clinical audiology to set the threshold level of a patient's cochlear implant processor. The separation of nerve responses from artifacts created by the stimulation signals and estimation of hearing thresholds from evoked potentials have in the past been carried out in a variety of different ways, e.g. often involving non-automatic procedure steps, e.g. the judgment of experts. Such non-automatic procedures can be time consuming and prone to errors. A review of efforts to identify and remove noise in eCAP-measurements has been published by [Undurraga et al.; 2012].

In general, measurement of eCAPs are used
  During an operation, where a cochlear implant part of a hearing assistance device is inserted, to test whether the stimulation of the cochlear implant is functioning well AND whether the nerve is responding. These facts must be verified before the operation is ended, hence requiring a reliable and fast measurement and verification procedure to minimize operation time.
  During fitting to determine hearing thresholds. Also here a fast and reliable method is preferable (although the time pressure is slightly less severe).

Thus there is a need for a reliable and fast method of identifying and processing electrically evoked (hearing) nerve responses.

DEFINITIONS

In general, a "hearing assistance device" refers to a device, such as e.g. a hearing aid or a listening device, which is adapted to improve, augment and/or protect the hearing capability of a user by receiving acoustic signals from the user's surroundings, generating corresponding (electric) audio signals, possibly modifying the audio signals, and providing the possibly modified audio signals as audibly sensed signals to at least one of the user's ears, e.g. (as in the present disclosure) in the form of electric signals transferred directly or indirectly to the cochlear nerve and/or to the auditory cortex of the user.

A hearing assistance device may in general comprise a single unit or several units communicating electronically with each other. Each of the one or more units of a hearing assistance device may be configured to be worn in any known way, e.g. behind the ear (BTE), at the ear, entirely or partly arranged in the pinna and/or in the ear canal, as an entirely or partly implanted unit, etc.

More generally, a hearing assistance device comprises an input transducer for receiving an acoustic signal from a user's surroundings and providing a corresponding (electric) input audio signal, a signal processing circuit for processing the input audio signal and an output unit for providing a signal perceivable as an acoustic signal to the user in dependence of the processed audio signal. Some hearing assistance devices may comprise multiple input transducers, e.g. for providing direction-dependent audio signal processing. In some hearing assistance devices, an amplifier may constitute the signal processing circuit. In some hearing assistance devices, the output unit may comprise one or more output electrodes for providing electric signals. In some hearing assistance devices, the output electrodes may be implanted in the cochlea and/or on the inside of the skull bone and may be adapted to provide the electric signals to the hair cells of the cochlea, to one or more auditory nerves and/or to the auditory cortex.

A "hearing system" refers to a system comprising one or two hearing assistance devices, and a "binaural hearing system" refers to a system comprising two hearing assistance devices and being adapted to (preferably cooperatively) provide audible signals to both of the user's ears. In a hearing system or a binaural hearing system, one or both of the hearing assistance devices may comprise other output unit in addition to output electrodes in order to provide audible signals e.g. in the form of acoustic signals radiated into the user's outer ears or acoustic signals transferred as mechanical vibrations to the user's inner ears through the bone structure of the user's head and/or through parts of the middle ear. In such hearing assistance devices, the output unit may comprise an output transducer, such as e.g. a loudspeaker for providing an air-borne acoustic signal or a vibrator for providing a structure-borne or liquid-borne acoustic signal. In an embodiment of a binaural hearing system, one of the hearing assistance devices comprises only such other output transducer (i.e. the output electrodes only present in one of the devices).

Hearing systems or binaural hearing systems may further comprise "auxiliary devices", which communicate with the hearing assistance devices and affect and/or benefit from the function of the hearing assistance devices. Auxiliary devices may be e.g. remote controls, remote microphones, audio gateway devices, mobile phones, public-address systems, car audio systems or music players. Hearing assistance devices, hearing systems or binaural hearing systems may in general be used for compensating for a hearing-impaired person's loss of hearing capability (as in the present disclosure), augmenting or protecting a normal-hearing person's hearing capability and/or conveying electronic audio signals to a person.

SUMMARY

An object of the present application is to improve identification and processing of recorded nerve response data in an implanted part of a hearing assistance device.

Objects of the application are achieved by the invention described in the accompanying claims and as described in the following.

A Hearing Assistance Device:

In an aspect of the present application, an object of the application is achieved by a hearing assistance device comprising an implanted part adapted for being implanted (in the head) at a user's ear, wherein the implanted part comprises A multitude of electrodes adapted for being located in the cochlea in proximity of an auditory nerve of the user;
Stimulation circuitry electrically coupled to a stimulation electrode during a stimulation time period and configured for applying a stimulation signal to the stimulation electrode;
Measurement circuitry electrically coupled to a recording electrode during a measurement time period and configured to measure a signal picked up by the recording electrode in response to said stimulation signal and providing a measured signal;
A control unit configured to control the timing of the application of the stimulation signal in the stimulation time period and to control the measurement time period relative to the stimulation time period; and
A processing unit configured to record the measured signal in the measurement time period and to identify a response from the auditory nerve based on said measured signal.

This has the advantage of reducing the bandwidth requirement of a communication link to an external part during fitting. A further advantage of embodiments of the disclosure is to reduce the processing time of identifying a nerve response.

When the implanted part is operationally implanted in a person, the electrodes are preferably located fully or partially in the cochlea of the person in a way allowing the electric stimulation signal to be applied to the auditory nerve and allowing a response signal to said stimulation (potentially) comprising a response from the nerve to be measured.

In an embodiment, the hearing assistance device comprises at least one external part and a communications link configured to allow exchange of data between the external and implanted parts of the device.

By locating the processing unit for identifying a response from the auditory nerve in the implanted part, communication between the implant and an external part (e.g. a BTE part) can be minimized (although at the cost of a more complex implant).

The term 'a stimulation signal' is on the present context taken to mean an electric stimulation signal, e.g. comprising one or more pulses, e.g. one or more biphasic pulses, e.g. current pulse provided by a current generator or voltage pulses provided by a voltage generator. The pulses are preferably of a configurable width in time and/or amplitude. In an embodiment, a stimulation pulse (for a given stimulation electrode) is configured to contain a predefined amount of electric energy determined in dependence of a current acoustic signal to be presented to a user and the sensitivity of the user's hearing nerve (at the stimulation electrode in question) to electric stimulation.

In an embodiment, the hearing assistance device (e.g. processing unit) is configured to compute at least one estimator of at least one statistical variable obtained from said measured signal. In an embodiment, the hearing assistance device (e.g. the processing unit) is configured to use the at least one statistical estimator to identify the response from the auditory nerve.

In an embodiment, the hearing assistance device is configured to generate signals or commands based on a criterion applied to said at least one estimator computed in the processing unit. In an embodiment, the processing unit and/or the control unit is configured to generate the signals or commands.

In an embodiment, the hearing assistance device comprises a wired or wireless interface to a fitting system.

In an embodiment, the processing unit and/or the control unit is configured to forward said signals or command to an external unit and/or to a fitting system via the communication link and/or via the wired or wireless interface.

In an embodiment, the hearing assistance device comprising a switch unit comprises a number of switching elements allowing each of said multitude of electrodes to be selected as a stimulation electrode and/or as a recording electrode at a given point in time.

Preferably the switch unit (and the number of switching elements) is controlled by the control unit. In an embodiment (e.g. in a specific nerve response measurement mode), the control unit is configured to control the stimulation unit and the switch unit to provide that one stimulation electrode at a time is selected for stimulation. In an embodiment (e.g. in a specific normal mode of operation), the control unit is configured to control the stimulation unit and the switch unit to provide that one or more stimulation electrodes are (or can be) selected for stimulation at a given time.

Preferably, the implanted part comprises a number of capacitors configured to provide that each of the multitude of electrodes are separated from the stimulation circuitry and the measurement circuitry by a capacitor (to avoid leak currents to induce electrolytic activity in the surrounding fluids).

In an embodiment, the control unit is configured to use said signals or commands to control (or influence) the stimulation unit and the switch unit (e.g. to repeat a measurement, to stop a measurement, to change an electrode, to change a stimulation signal, etc.).

In an embodiment, the control unit is configured to identify said response from the auditory nerve for a given stimulation electrode for a number of different levels of the stimulation signal, and to determine a threshold level of stimulation from said responses from the auditory nerve.

Preferably, the processing unit of the implanted part is capable of using statistical criteria to analyze nerve responses to stimulation, the implanted part is e.g. capable of identifying whether or not an eCAP is present in response to a given stimulation signal (on a given stimulation and recording electrode). Preferably, the implanted part is capable of forwarding such information to a fitting system (e.g. software running on a PC) via a wired or wireless interface. Depending on whether or not an eCAP is present, the fitting system may be configured to modify the stimulation (e.g. either change stimulation level, stop recording the eCAP, requesting a change of stimulation and/or recording electrode, etc.). Alternatively, the control unit of the implanted part is configured to perform these actions, thereby allowing the implanted part (e.g. a fully implanted hearing assistance device) to automatically adjust the stimulation in dependence of a measured eCAP signal, thereby providing an automated fitting procedure and/or an automated update procedure. The update procedure adapting the present stimulation signal (e.g. its level/intensity) of a selected stimulation electrode to a current hearing capability (as indicated by a nerve response to electric stimulation) is e.g. performed automatically at regular intervals, e.g. dynamically.

In an embodiment, a measured signal representing a nerve response to a biphasic stimulation pulse comprises (corresponding) first negative (with minimum $N_1$) and positive peaks (with maximum $P_1$). Preferably, the processing unit is configured to provide that the at least one estimator of at least one statistical variable obtained from said measured signal for determining a response from an auditory nerve (e.g. an eCAP) is based on a-priori knowledge of said measured signal. In an embodiment, the a-priori knowledge of said measured signal comprises knowledge of latency times of the occurrence of said peak nerve responses after a stimulation pulse (cf. also FIG. 4). Thereby the nerve response identification is restricted to a peak search of the clinical range the measured signal. An advantage of using the estimator is that it allows for better detection, independently of the signal to noise ratio (SNR). Furthermore, it is computationally relatively simple. The present scheme further paves the way for improved embedded real-time nerve response (e.g. eCAP) detection.

In an embodiment, the signals or commands generated by the processing unit and/or the control unit is transmitted to an external, non-implanted device (e.g. an external processor or a fitting system), and further processed before being transmitted back to the implanted part. In an embodiment, the signals or commands generated by the processing unit and/or the control unit remains in the implantable part (is not transmitted to an external part or a fitting system).

In an embodiment, the hearing assistance device comprises a reference electrode adapted for being located outside the cochlea. In an embodiment, the hearing assistance device (e.g. the control unit) is configured to provide that the stimulation electrode is the same as the recording electrode. In an embodiment, the hearing assistance device (e.g. the control unit) is configured to provide that the stimulation electrode and the recording electrode are two physically different entities.

In an embodiment, the hearing assistance device (e.g. the control unit) is configured to provide that the stimulation time period and the measurement time period are consecutive in time. In other words, in such embodiment, the stimulation time period and the measurement time period are complimentary (do not overlap) in time. Alternatively, an overlap (e.g. a partial or full overlap) in time between the stimulation time period and the measurement time period may exist, e.g. in case the stimulation electrode and the recording electrode are two different electrodes, and/or if other signals than the eCAPs are measured, e.g. eABRs or other brain evoked potentials.

Preferably, the measurement circuitry is configured to comprise at least one analogue component.

In an embodiment, the measurement circuitry comprises an analogue comparator comprising first and second inputs and an output representing a comparison of the first and second inputs, wherein the first input is operationally coupled to said recording electrode during said measurement time period, controlled by the control unit.

The analogue comparator is preferably a voltage comparator configured to compare (e.g. determine a difference between) two voltages present at its two inputs. In an embodiment, the analogue comparator comprises an operational amplifier. In an embodiment, the analogue comparator is constituted by an operational amplifier, preferably an operational amplifier based voltage comparator. In an embodiment, the measurement circuitry comprises a digital comparator. In an embodiment, the measurement circuitry comprises a current comparator In an embodiment, the processing unit comprises a digital processor and an AD-DA-interface to said analogue comparator, the AD-DA-interface having an analogue input and an analogue output. Preferably, the AD-DA-interface to the at least one analogue component comprises an analogue to digital (A/D) converter and a digital to analogue (D/A) converter. In an embodiment, the analogue output of the AD-DA-interface is operationally coupled to the second input of the analogue comparator. In an embodiment, the output of the analogue comparator is operationally coupled to an analogue input of the AD-DA-interface of the processing unit. In an embodiment, the AD-DA interface comprises a variable amplifier for amplifying an input to the AD-DA interface.

Preferably, when the measurement is performed on an artifact-free signal (e.g. an artifact-corrected measured signal resulting from the cancellation performed by the analogue comparator), the artifact free signal can be amplified to increase the recording gain. This solution balances the tradeoff between gain and bandwidth when recording small signals. Much smaller nerve or evoked potential signals can thus be recorded by the processing unit than if the recording unit was directly sampling a signal from the recording electrode. Preferably, the variable amplification is controlled by the control unit depending on the current type of measurement. Preferably, the amplification of the variable amplifier is relatively low during a measurement of the artifact. Preferably, the amplification of the variable amplifier is relatively high during a measurement of the nerve response. In an embodiment, the output of the analogue comparator is operationally coupled to an input of an A/D-converter (e.g. via a variable amplifier). Preferably, the A/D converter comprises a variable amplifier.

An advantage of the method is that the measurement is performed in the analogue domain so that a combination of subtraction and amplification is provided by the analogue comparator (e.g. an operational amplifier), whereas the processing unit is configured to process the analogue measurement results in the digital processor after conversion in an A/D converter. Thereby the analogue and digital signal processing is combined to utilize the strengths of each domain (technology) in an optimal and relatively simple way.

The processing unit is preferably configurable to allow the extraction of other signals than the direct response of the nerve cells in cochlea. This can e.g. be achieved by changing the sample rate (and possibly amplification) of the A/D-converter, whereby signals from other parts of the nerve system between cochlea and the hearing centre of the brain can be extracted. The planned system thus provides a platform for artifacts subtraction and embedded recordings of auditory evoked potentials regardless of their origin (nerve: ECAP, auditory brainstem: EABR, auditory cortex: MLR & AECP).

In an embodiment, the stimulation circuitry is configured to provide that the stimulation signal comprises one or more stimulation pulses. Preferably, the a stimulation pulse is biphasic. A biphasic pulse comprises a positive pulse followed by a negative pulse or a negative pulse followed by a positive pulse.

In an embodiment, the control unit is configured to provide that the stimulation time period at least comprises the time period from the start or the first of said one or more stimulation pulses to the end of the last of said one or more stimulation pulses. In an embodiment, the stimulation circuitry is configured to provide that a first stimulation signal comprises two stimulation pulses, a masker pulse and a probe pulse separated by a predefined masker-probe time interval. Preferably, the masker-probe time interval is larger than the latency time of the auditory nerve (to ensure that a (first) response of the auditory nerve to the masker pulse has occurred before the probe pulse starts). The latency time is defined as the time from the start of the stimulation pulse until a measureable electric potential (eCAP) is generated by the auditory nerve. The latency for the auditory nerve is e.g. of the order of 200-300 μs. The latency is generally far longer than the duration of a typical biphasic stimulation pulse (e.g. of the order of 20 μs per stimulation phase i.e. of the order of 40 μs for biphasic pulse).

In an embodiment, the control unit is configured to initiate a first measurement in a first measurement time period at a first predefined maximum time after the start of the probe pulse of said first stimulation signal. A first measurement (e.g. of the artifact) is preferably performed in the or each first measurement time period. Preferably, the predefined time after the initiation of the last stimulation pulse is smaller than the latency time of the auditory nerve (to ensure that the measurement time period includes the time period where a nerve response can normally be expected).

Preferably, the measurement circuitry is—e.g. in a specific artifact-averaging mode—configured to compare an analogue representation of a currently recorded analogue signal from a recording electrode with a predefined, e.g. constant signal, and to provide a current analogue measurement result. In an embodiment, the current analogue measurement result is fed to the AD-DA-interface of the processing unit for being processed in the digital processor or for being transmitted to an external part and/or to a fitting system via a communication interface.

In an embodiment, the stimulation circuitry is configured to provide a number (or series) of first stimulation signals occurring after each other with a predefined time interval without stimulation pulses between each first stimulation signal. In other words, the stimulation circuitry is configured to generate a stream of subsequent occurrences of (pairs of) a masker pulse and a probe pulse (the masker pulse and the probe pulse being separated by a predefined masker-probe time interval (MPI)), each masker-probe pulse pair being separated by a predefined time interval without any stimulation pulses. Preferably, the control unit is configured to initiate a first measurement after each occurrence of a masker probe pair (including the mentioned predefined time interval without stimulation pulses). In an embodiment, the control unit is configured to provide that the second input to the analogue comparator (e.g. the output of the AD-DA-interface, e.g. a D/A converter) is set to a constant level (e.g. zero or GND) during said first measurement time period. Thereby the measured signal (MP), which represents only a transient of the first stimulation signal (artifact), is directly measured Preferably, the measurement results of each of the first measurement time periods are averaged over time in the digital processor, whereby an average artifact is provided (digital average $<MP>_D$).

In an embodiment, the stimulation circuitry is configured to provide that a second stimulation signal comprises one stimulation pulse, a probe pulse, and wherein the control unit is configured to initiate a second measurement in a second measurement time period at a second predefined maximum time after the initiation of the probe pulse of said second stimulation signal.

Preferably, the measurement circuitry is—e.g. in a specific nerve response measurement mode—configured to compare an analogue representation of a currently recorded analogue signal (e.g. analogue signal $P_A(t)$ (t being time) from a probe pulse) from a recording electrode with a processed analogue signal from the processing unit (e.g. an analogue version ($<MP>_D)_A$ of digital average artifact $<MP>_D$) and to provide a current analogue measurement result (e.g. $eCAP_A = P_A(t) - (<MP>_D)_A$). In an embodiment, the current analogue measurement result is fed to the AD-DA-interface of the processing unit (e.g. providing digital eCAP-signal $(eCAP_A)_D(t)$) for being processed (e.g. averaged, and/or subject to a statistical estimator) in the digital processor or for being transmitted to an external part and/or to a fitting system via a communication interface.

In an embodiment, the first and second predefined maximum times are identical.

In an embodiment—in a specific nerve response measurement mode, during the second measurement time period—where the measured signal from the recording electrode represents the transient of the probe pulse plus a nerve response, the processing unit and/or the control unit is configured to provide that a resulting averaged or otherwise determined artifact value from the processing unit is fed to the second input of the analogue comparator via the AD-DA-interface, whereby the output of the analogue comparator represents the nerve response.

In the specific nerve response measurement mode—during the second measurement time period—a resulting averaged artifact value from the processing unit is fed to the second input of the analogue comparator (via the AD-DA-interface). The measured signal from the recording electrode (originating from a second measurement time period) represents the transient of the probe pulse (artifact) plus the nerve response (e.g. an eCAP). Hence, the output of the analogue comparator represents the nerve response (if any)

In an embodiment, the determination of the nerve response is refined by one or more further measurements in one or more further measurement time periods, allowing e.g. a transient of the masker pulse (M) (cf. e.g. FIG. 4a) and/or a bias level to be subtracted from the measured nerve response signal (to further isolate the nerve response, cf. e.g. [Undurraga et al.; 2012]).

In an embodiment, the processing unit is configured to compute estimators of one or more statistical variables from said measurement signals obtained after either the first or second (and/or further) measurement periods.

In an alternative embodiment, instead of calculating an average artifact as described, the artifact is estimated in an off-line procedure in advance of the use of the implant part of the hearing assistance device, e.g. by simulation. In an embodiment, the processing unit comprises a memory comprising tables of relevant artifacts (as a function of pulse amplitude), i.e. A(t), $t=t_{M,start}-t_{M,end}$.

In an embodiment, the processing unit and/or the control unit is configured to transmit said identified nerve response from the auditory nerve to a fitting system and/or to an external part via a communication interface.

In an embodiment, the processing unit and/or the control unit is configured to compared an estimator of one or more statistical variables are against a pre-defined criterion, which decides whether the processing unit forwards a signal or a command to an external part and/or to a fitting system. In an embodiment, the nerve response is transmitted to the external part and/or to the fitting system along with the estimator of one or more statistical variables. These estimators can e.g. be used to testify the reliability of the identified nerve response.

In an embodiment, the processing unit of the implanted part is configured to identify a nerve response by means of a restricted peak-picking algorithm using a-priori information of the nerve response. The nerve response is assumed to comprise a positive peak component ($P_1$) having positive peak latencies in the time interval between a minimum $I_{P1}$ and a maximum $L_{P1}$ latency and a negative peak component ($N_1$) having peak latencies in the interval $I_{N1}$ and $L_{N1}$. The nerve response amplitude is taken to be MAX(s($I_{P1}$<t<$L_{P1}$))–MIN(s($I_{N1}$<t<$L_{N1}$), where s(t) is a measured signal, and t is time. MAX and MIN represent algorithms for finding a maximum and a minimum value, respectively, in a data set.

In a further embodiment, the processing unit of the implanted part is configured to compare the nerve response amplitude to the same estimator computed for the artifact-only recording period. In a further embodiment, the nerve response amplitude is taken to be MEAN(s($I_{P1}$<t<$L_{P1}$))–MEAN(s($I_{N1}$<t<=$L_{N1}$)). MEAN represents e.g. an algorithm for finding a mean (e.g. an average) value of a data set.

In an embodiment, the hearing assistance device is adapted—during a normal mode of operation—to provide a frequency dependent gain to compensate for a hearing loss of a user.

In an embodiment, the hearing assistance device comprises an input transducer for converting an input sound to an electric input signal. In an embodiment, the hearing assistance device comprises a directional microphone system adapted to enhance a target acoustic source among a multitude of acoustic sources in the local environment of the user wearing the hearing assistance device. In an embodiment, the directional system is adapted to detect (such as adaptively detect) from which direction a particular part of the microphone signal originates. This can be achieved in various different ways as e.g. described in the prior art.

In an embodiment, the hearing assistance device further comprises other relevant functionality for the application in question, e.g. compression, noise reduction, etc. Various aspects of digital hearing aids and relevant processing algorithms are described in [Schaub; 2008]. Various aspects of cochlear implant type hearing aids are described in [Clark; 2003].

Use:

In an aspect, use of a hearing assistance device as described above, in the 'detailed description of embodiments' and in the claims, is moreover provided. In an embodiment, use of a hearing assistance device comprising an implanted part is provided.

A Method:

In an aspect, a method of operating a hearing assistance device comprising an implanted part adapted for being implanted (in the head) at a user's ear, the implanted part comprising a multitude of electrodes adapted for being located in the cochlea in proximity of an auditory nerve of the user is furthermore provided by the present application. The method comprises
- electrically coupling stimulation circuitry to a stimulation electrode during a stimulation time period and applying a stimulation signal to the stimulation electrode;
- electrically coupling measurement circuitry to a recording electrode during a measurement time period and measuring a signal picked up by the recording electrode in response to said stimulation signal and providing a measured signal;
- controlling the timing of the application of the stimulation signal in the stimulation time period and the measurement time period relative to the stimulation time period;
- identifying a response from the auditory nerve based on said measured signal.

It is intended that some or all of the structural features of the hearing assistance device described above, in the 'detailed description of embodiments' or in the claims can be combined with embodiments of the method, when appropriately substituted by a corresponding process and vice versa. Embodiments of the method have the same advantages as the corresponding hearing assistance devices.

In an embodiment, the step of modifying the electrical stimulation is arranged to depend on whether a response from the auditory nerve was identified or not.

In an embodiment, the step of identifying a response from the auditory nerve based on said measured signal comprises an averaging procedure wherein a number of measured signals from the recording electrode is averaged.

Electrically evoked compound action potentials (eCAPs) are routinely used in clinical audiology to set the threshold level of a patient's cochlear implant processor. But the estimation of threshold from evoked potentials is often left to the judgment of experts, which can be time consuming. The hearing assistance device and corresponding method of the present disclosure cochlear provides a scheme for embedding advanced real-time computation capabilities to perform real-time signal processing on eCAP measurements in an implanted part before returning nerve response estimates and/or stimulation threshold values to the fitting system by telemetry (communication interface).

In an embodiment, the step of identifying a response from the auditory nerve based on the measured signal comprises a statistical identification algorithm for identifying a nerve response based on priori knowledge of the measured signal.

In a preferred embodiment, prior knowledge on eCAP latency, amplitude and shape is systematically utilized to produce a robust estimate of patient (hearing) thresholds. An eCAP detection algorithm using a threshold criterion based on a likelihood ratio test has been designed.

In an embodiment, the nerve response identification algorithm comprises a restricted peak-picking algorithm using a-priori information of the nerve response, assumed to comprise a positive peak component ($P_1$) having positive peak latencies in the time interval between a minimum $I_{P1}$ and a maximum $L_{P1}$ latency and a negative peak component ($N_1$) having peak latencies in the interval $I_{N1}$ and $L_{N1}$, and the nerve response amplitude is taken to be MAX(s($I_{P1}$<t<$L_{P1}$))–MIN(s($I_{N1}$<t<$L_{N1}$), where s(t) is a measured signal, and t is time. MAX and MIN represent algorithms for finding a maximum and a minimum value, respectively, in a data set.

In a further embodiment, the nerve response amplitude is compared to the same estimator computed for the artifact-only recording period. In a further embodiment, the nerve response amplitude is taken to be MEAN(s($I_{P1}$<t<$L_{P1}$))–MEAN(s($I_{N1}$<t<=$L_{N1}$). MEAN represents an algorithm for finding a mean (e.g. an average) value of a data set.

A Listening System:

In a further aspect, a listening system comprising a hearing assistance device as described above, in the 'detailed description of embodiments', and in the claims, AND an auxiliary device is moreover provided.

In an embodiment, the system is adapted to establish a communication link between the hearing assistance device and the auxiliary device to provide that information (e.g. control and status signals, possibly audio signals) can be exchanged or forwarded from one to the other.

In an embodiment, the auxiliary device is or comprises an audio delivery device, e.g. an audio gateway device adapted for receiving a multitude of audio signals (e.g. from an entertainment device, e.g. a TV or a music player, a telephone apparatus, e.g. a mobile telephone or a computer, e.g. a PC) and adapted for selecting and/or combining an appropriate one of the received audio signals (or combination of signals) for transmission to the hearing assistance device. In an embodiment, the auxiliary device is or comprises a remote control for controlling functionality and operation of the hearing assistance device(s). In an embodiment, the auxiliary device is or comprises a telephone, e.g. a Smartphone.

In an embodiment, the auxiliary device is another hearing assistance device. In an embodiment, the listening system comprises two hearing assistance devices adapted to implement a binaural listening system, e.g. a binaural hearing aid system.

Further objects of the application are achieved by the embodiments defined in the dependent claims and in the detailed description of the invention.

As used herein, the singular forms "a," "an," and "the" are intended to include the plural forms as well (i.e. to have the meaning "at least one"), unless expressly stated otherwise. It will be further understood that the terms "includes," "comprises," "including," and/or "comprising," when used in this specification, specify the presence of stated features, integers, steps, operations, elements, and/or components, but do not preclude the presence or addition of one or more other features, integers, steps, operations, elements, components, and/or groups thereof. It will also be understood that when an element is referred to as being "connected" or "coupled" to another element, it can be directly connected or coupled to the other element or intervening elements may be present, unless expressly stated otherwise. Furthermore, "connected" or "coupled" as used herein may include wirelessly connected or coupled. As used herein, the term "and/or" includes any and all combinations of one or more of the associated listed items. The steps of any method disclosed herein do not have to be performed in the exact order disclosed, unless expressly stated otherwise.

BRIEF DESCRIPTION OF DRAWINGS

The disclosure will be explained more fully below in connection with a preferred embodiment and with reference to the drawings in which.

The figures are schematic and simplified for clarity, and they just show details which are essential to the understanding of the disclosure, while other details are left out.

Further scope of applicability of the present disclosure will become apparent from the detailed description given hereinafter. However, it should be understood that the detailed description and specific examples, while indicating preferred embodiments of the disclosure, are given by way of illustration only. Other embodiments may become apparent to those skilled in the art from the following detailed description.

DETAILED DESCRIPTION OF EMBODIMENTS

Figure 1A:
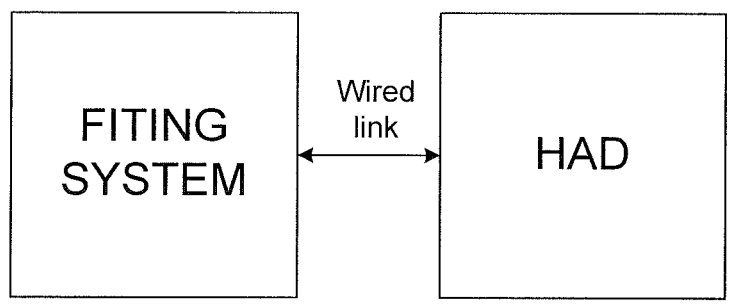
FIG. 1a and FIG. 1b schematically show a fitting system operationally coupled to a hearing assistance device, either by a wired communication link (FIG. 1a) or by a wireless communication link (FIG. 1b), FIG. 2a, FIG. 2b, and FIG. 2c schematically show various partitions of a hearing assistance device according to the present disclosure, in FIG. 2a a hearing assistance device in its most basic form comprising only an (self-contained) implanted part, in FIG. 2b a hearing assistance device comprising an implanted part and an external part with a wireless communication link between them, and in FIG. 2c a hearing assistance device as in FIG. 2b but where the external part comprises an antenna part for establishing the wireless link to the implanted part and a processing part for processing an audio signal, and where the antenna and processing parts are connected by a wired link (e.g. a cable)
Figure 1B:
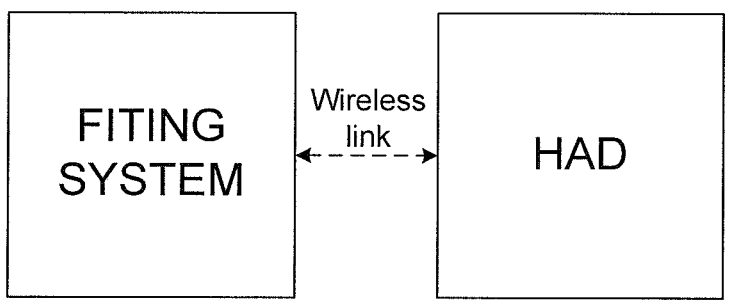

FIG. 1 shows a FITTING SYSTEM operationally coupled to a hearing assistance device (HAD), either by a wired communication link (Wired link, FIG. 1a) or by a wireless communication link (Wireless link, FIG. 1b). The FITTING SYSTEM is preferably configured to initiate the application of an appropriate stimulation signal (e.g. comprising different stimulation intensities) to a selected electrode of an implanted part of the hearing assistance device and to receive a resulting nerve response from a processing unit of the implanted part. The FITTING SYSTEM is preferably further configured—based on said resulting nerve response(s)—to determine a threshold intensity level (T) (for a selected electrode) above which a user can perceive a stimulation as a sensation of sound. Alternatively, the threshold intensity level may be determined in the implanted part and optionally forwarded to the FITTING SYSTEM.

Figure 2A:
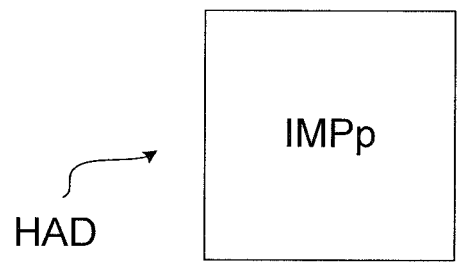
Figure 2B:
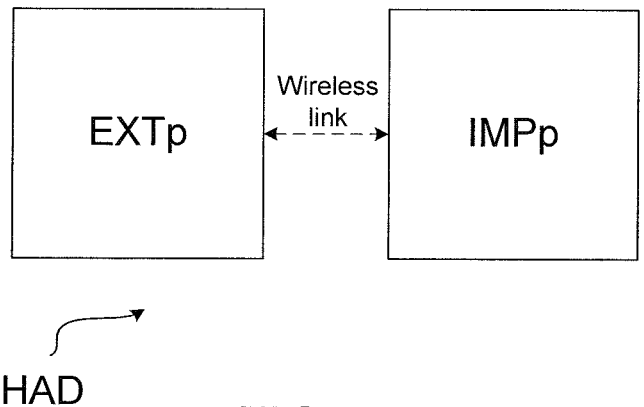
Figure 2C:
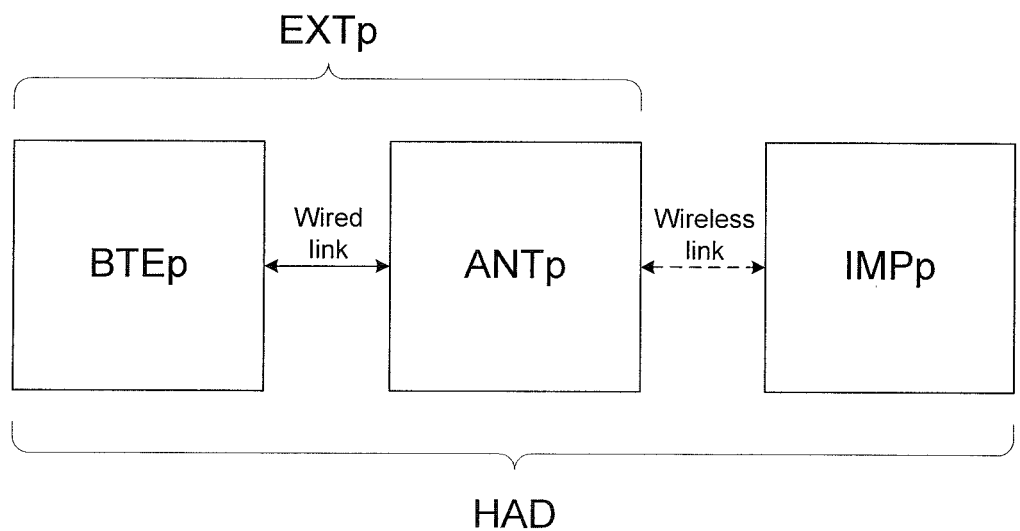

FIG. 2 shows various partitions of a hearing assistance device according to the present disclosure. FIG. 2a shows a hearing assistance device (HAD) in its most basic form comprising only a, preferably self-contained (e.g. battery driven, and comprising an input transducer, e.g. a microphone, and appropriate processing capability), implanted part (IMPp). FIG. 2b shows a hearing assistance device (HAD) comprising an implanted part (IMPp) and an external part (EXTp) with a wireless (e.g. inductive) communication link (Wireless link) between them. The external part (EXTp) may e.g. comprise an input transducer, e.g. a microphone, and a signal processing unit for enhancing a received electric input signal and possibly for preparing a scheme for stimulating electrodes of the implanted part (IMPp) in dependence of the current input signal. The external part (EXTp) may further comprise antenna and transceiver circuitry for transferring stimulation information (and possibly corresponding energy) to the implanted part (IMPp) (which comprises corresponding antenna and transceiver circuitry to allow reception of the transmitted signals and energy, to establish the Wireless link). FIG. 2c shows a hearing assistance device (HAD) as in FIG. 2b but where the external part (EXTp) comprises an antenna part (ANTp) for establishing the wireless link to the implanted part (IMPp) and a processing part (BTEp) for processing an audio signal, and where the antenna and processing parts are connected by a wired link (Wired link, e.g. a cable). An embodiment of FIG. 2c is shown in further detail in FIG. 3.

Figure 3:
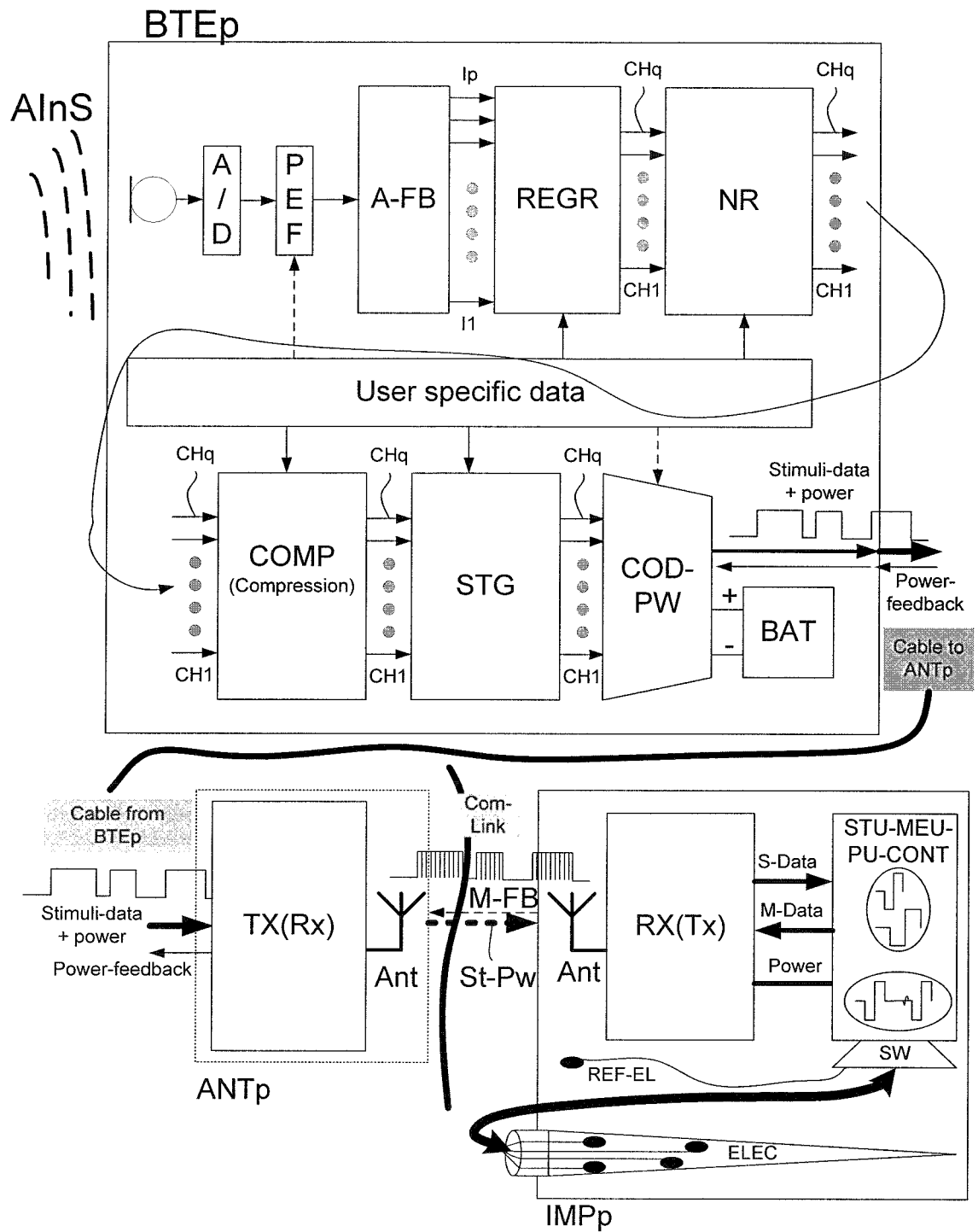
FIG. 3 shows a further detailed embodiment of the hearing assistance device of FIG. 2c, FIG. 4a, FIG. 4b, and FIG. 4c schematically show exemplary steps in the electric stimulation of the auditory nerve and a measurement of a nerve response resulting from the stimulation, FIG. 4a illustrating the measurement of a transient of a masker stimulation pulse (M), FIG. 4b illustrating the measurement of a transient of a masker followed by probe stimulation pulse (MP), and FIG. 4c illustrating the measurement of a nerve response and a transient of a probe stimulation pulse (P), FIG. 5 schematically shows an embodiment of a stimulation, measurement and processing part of an implanted part of a hearing assistance device according to the present disclosure, FIG. 6 schematically shows an embodiment of implanted part of a hearing assistance device according to the present disclosure, and FIG. 7 schematically illustrates parameters of a statistical estimator of a nerve response utilizing prior knowledge of peak latencies.

FIG. 3 shows an embodiment of a hearing assistance device according to the present disclosure. FIG. 3 illustrates a 'normal operation scenario', where electrodes (ELEC) of the implanted part (IMPp) are stimulated according to an acoustic input signal (AInS) picked up by a microphone of an external part of the system (here external part BTEp, e.g. adapted for being located behind an ear of a user), the relevant current stimulation scheme generated in the external BTEp part and the accompanying necessary electric energy being transferred to the implanted part via a communication link (Com-Link) between the implanted part (IMPp) and an external antenna part (ANTp).

The external BTEp part comprises a forward signal path comprising:
a microphone,
an A/D converter (A/D) for converting an analogue input signal to a digital signal by sampling the analogue input signal with a sampling frequency $f_s$,
a pre-emphasis filter (PEF) (e.g. a FIR filter) for adapting the input levels to a loudness perception of a normally hearing person (psychoacoustic adaptation),
an analysis filter bank (A-FB) for converting a single time variant input signal to time-variant signals in a number p of frequency bands ($I_1:I_p$). The analysis filter bank may e.g. comprise a 128 point FFT providing p=64 frequency bands (or alternatively a filter bank followed by an envelope detector),
a regrouping unit (REGR) for allocating p frequency bands to a number q of channels ($CH_1:CH_q$) equal to the number of electrodes used, e.g. q=20, configurable based on user data (cf. unit User specific data), e.g. based on the Bark scale or 'critical bands'),
a noise reduction algorithm (NR, based on User specific data) adapted to attenuate signal components that are judged not to be part of a target signal, the noise reduction algorithm e.g. working independently on signals of each channel ($CH_1:CH_q$),
a compression scheme (COMP, based on User specific data) adapted to provide a level dependent compression of an input signal of each channel ($CH_1:CH_q$),
a stimulation generator (STG) for generating a representation of the stimuli of each channel ($CH_1:CH_q$), the stimuli for a given channel corresponding to a given intensity in a given frequency range at a given point in time (reflecting the current input audio signal) to be applied to corresponding electrodes of the implanted part,
a local energy source (BAT), e.g. a battery, such as a rechargeable battery for energizing components of the hearing assistance device (BTEp, ANTp, IMPp), and
a stimulus data coding unit (COD-PW, based on User specific data) for generating a scheme (incl. providing energy for stimulating each of the (active) electrodes (ELEC, max q electrodes, typically less) of the implanted part (IMPp), and forwarding stimuli (or coded stimuli) and energy via a cable to the antenna part (ANTp).

The unit User specific data) may represent user data stored in a memory of the BTEp part or user data read into the various algorithms during a fitting session (or a combination of the two).

In an alternative embodiment, the components of the external part (BTEp) are included in the implanted part (IMPp), whereby the hearing assistance device is self-contained (cf. FIG. 2a). In such an embodiment, only a communication link to a fitting system is necessary.

In the embodiment of FIG. 3, a cable (denoted Cable to ANTp, and Cable from BTEp, in the BTEp- and ANT-p-ends, respectively) connects the BTE-part (BTEp) to the antenna part (ANTp) and providing separate digital data and power (denoted Stimuli-data+power) to the antenna part (ANTp).

The antenna part (ANTp) is adapted for being located at the ear of the user allowing a communication link (Com-link) to be established with the implanted part (IMPp). The antenna part comprises:
a power and data mixing unit (e.g. incl. a crystal oscillator) forming part of an inductive transmitter (and backlink receiver), (TX (Rx)) and antenna coil (Ant).

The implanted part (IMPp) comprises:

an inductive antenna coil (Ant) and receiver (and backlink transmitter), (RX(Tx)), a carrier with a multitude of electrodes (ELEC), each being separated from a current source of a stimulation unit (STU) and a voltage measurement unit (units VM and COMP in FIG. 5) for capturing a nerve response by a capacitor (cf. Capacitor in FIG. 5):

a stimulation unit (STU) comprising a data extraction circuit, for extracting configuration data and stimuli data a current generator for generating a stimulus current (based on the extracted stimulus data) to be applied to the electrodes (ELEC), an interface to the electrodes comprising capacitors and switches (SVV) for switching between individual electrodes and their connection to the stimulation unit (STU) and to a measurement unit (MEU), an operational amplifier (COMP in FIG. 5, forming part of a measurement unit MEU in FIG. 6) and a processing unit (PU) (comprising a digital processor (DSP in FIG. 5) for processing and identifying nerve response measurements (e.g. eCAPs), and a control unit (CONT) configured to control the timing of the application of stimulation signals in a stimulation time period and the coupling (via switch unit (SVV)) of a relevant stimulation electrode to the stimulation unit (STU) and the measurement of a resulting response in the measurement time period and the coupling (via switch unit (SVV)) of a relevant recording electrode to the measurement unit (MEU).

An inductive, preferably bi-directional, communication link (Com-link) (e.g. comprising a 4 MHz carrier) is established by the inductive coils (Ant) of the antenna part (ANTp) and the implanted part (IMPp) when the two located in an operational position (near the ear, on each side of the skin of a person). A back-link from the implant part to the antenna- (and BTE-) part is based on 'load communication'. Due to the inductive coupling between the two antenna coils, any draw of current in the implanted part can be sensed in the antenna part. Thereby data-messages can be transmitted to the processor of the BTE-part (e.g. implant status signals (e.g. power level), electrode measurement data (impedances, and eCAPs). The backlink data can e.g. be coded in the signal using pulse width modulation (PWM). Alternatively, a digital coding scheme can be applied The external parts (BTEp and ANTp) can be partitioned in any other appropriate way than shown in FIG. 3. In an embodiment, the output of the BTE part (BTEp) are a) digitally coded data representing the electrode stimuli and b) a battery voltage, whereas the antenna part (ANTp) comprises a 4 MHz crystal oscillator whose output is mixed with the coded data to provide an on-off-coded signal, which is transmitted to the implant receiver via the inductive link.

In a fitting situation or during operation, the nerve responses (e.g. eCAPs) and/or electrode impedance measurements are communicated to a fitting system for setting up the hearing assistance device according to a user's particular needs, either directly via the antenna part (ANTp) or via the BTE part (BTEp).

The analogue electric signal representing an acoustic signal from the microphone is converted to a digital audio signal in the analogue-to-digital converter (A/D). The analogue input signal is sampled with a predefined sampling frequency or rate $f_s$, $f_s$ being e.g. in the range from 8 kHz to 48 kHz (adapted to the particular needs of the application) to provide digital samples $x_n$ (or x[n]) at discrete points in time $t_n$ (or n), each audio sample representing the value of the acoustic signal at $t_n$ by a predefined number $N_s$ of bits, $N_s$ being e.g. in the range from 1 to 16 bits. A digital sample x has a length in time of $1/f_s$, e.g. 50 µs, for $f_s$=20 kHz. In an embodiment, a number of audio samples are arranged in a time frame. In an embodiment, a time frame comprises 64 audio data samples. Other frame lengths may be used depending on the practical application.

In an embodiment, the analysis filter bank (A-FB) comprise(s) a TF-conversion unit for providing a time-frequency representation of an input signal. In an embodiment, the time-frequency representation comprises an array or map of corresponding complex or real values of the signal in question in a particular time and frequency range. In an embodiment, the TF conversion unit comprises a filter bank for filtering a (time varying) input signal and providing a number of (time varying) output signals each comprising a distinct frequency range of the input signal. In an embodiment, the TF conversion unit comprises a Fourier transformation unit for converting a time variant input signal to a (time variant) signal in the frequency domain. In an embodiment, the frequency range considered by the hearing assistance device from a minimum frequency $f_{min}$ to a maximum frequency $f_{max}$ comprises a part of the typical human audible frequency range from 20 Hz to 20 kHz, e.g. a part of the range from 20 Hz to 8 kHz or 12 kHz.

Figure 4A:
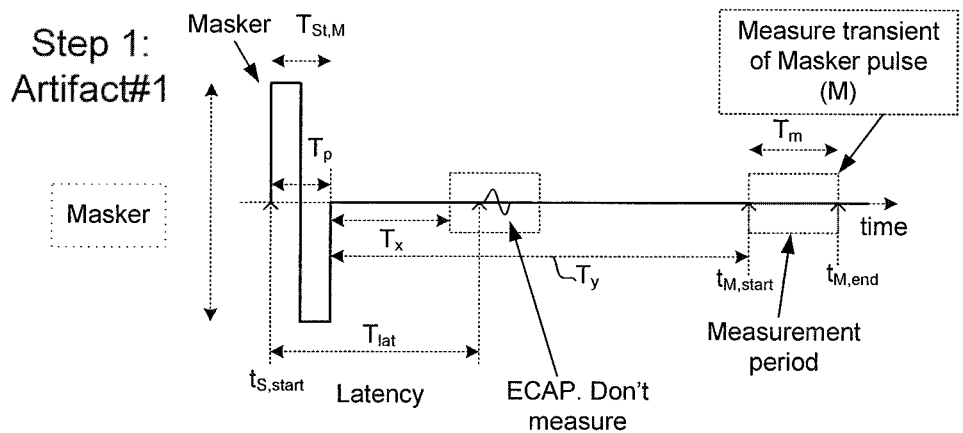
Figure 4B:
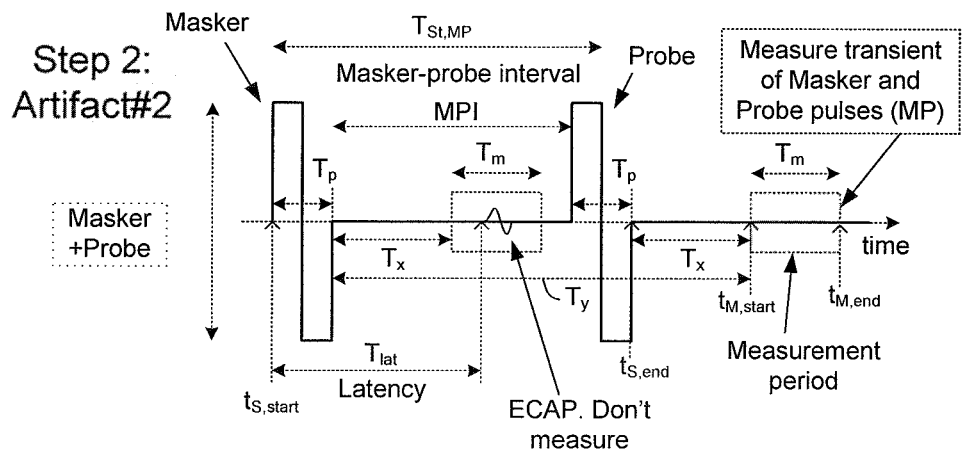
Figure 4C:
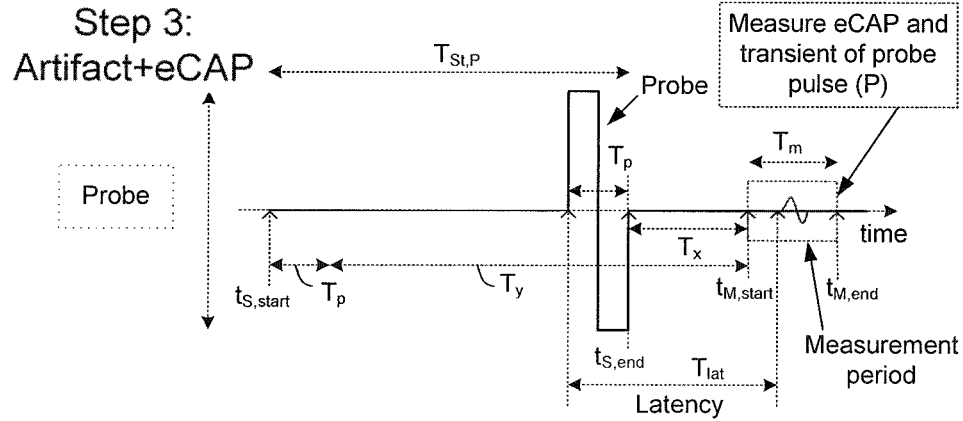

FIG. 4 shows exemplary steps in the electric stimulation of the auditory nerve and a measurement of a nerve response resulting from the stimulation. The separate measurements of first (Step 1: Artefact #1) and second artifacts (alone) (Step 2: Artefact #2) and artifact plus ECAP (Step 3: Artifact+eCAP) are illustrated in FIGS. 4a, 4b and 4c, respectively.

FIG. 4a illustrates the measurement of a transient of a masker stimulation pulse (M). FIG. 4b illustrates the measurement of a transient of a masker followed by probe stimulation pulse (MP). FIG. 4c illustrates the measurement of a nerve response and a transient of a probe stimulation pulse (P). As schematically indicated in FIG. 4a, a transient response from a masker pulse (M) is measured in a specific Measurement period. As shown in FIG. 4b, the transient of the combination of masker (M) plus probe (P) pulse signal that remains at the recording window (Measurement period) is likewise measured. Finally, the nerve response resulting from the probe pulse (and a transient of the probe pulse) as illustrated ion FIG. 4c is likewise recorded in the Measurement period. The same procedure is discussed in connection with FIG. 2 of [Undurraga et al.; 2012], where ECAP (t)=M(t)+P(t)−MP(t) is determined. Thereby the term M(t)−MP(t) ideally only represents the (negative of the) transient response of the probe pulse, so that P(t)+[M(t)−MP(t)] represents the nerve response (ECAP) alone.

An electric stimulation pulse on an electrode close to a nerve results in a measureable electric potential (eCAP), but it comes with a certain latency time, $T_{lat}$, relative to the start, $t_{S,start}$, of the stimulation pulse (cf. e.g. FIG. 4a, 4b). The latency is of the order of 200-300 µs. The latency time is typically far longer than the duration $T_p$ of a typical biphasic stimulation pulse (e.g. of the order of 40 µs). The nerve has a certain refractory period after a stimulation in which it cannot respond to a new stimulus. The refractory period is divided in an absolute and a relative refractory period. In the absolute refractory period, which is of interest here, no (second) nerve response is observed irrespective of the size of the stimulus. The absolute refractory period of an auditory nerve is e.g. of the order of 0.5 ms to 1 ms. To ensure that only the (transient part of the) stimulus remains in a Measurement period after a first (Masker, M) pulse and a second (Probe, P) pulse have been applied to an electrode (as in FIG. 4b), the time elapsed between the two pulses (the so-called Masker Probe Interval, MPI) should be shorter than the (absolute) refractory period, as illustrated in Step 2 (the Artifact #2 measurement) of FIG. 4b. On the other hand, to ensure that a (first) response of the auditory nerve to the Masker pulse (M) has occurred before the Probe pulse starts (cf. FIG. 4b), the masker-probe time interval (MPI) is configured to be larger than the latency time $T_{lat}$ of the auditory nerve. The implanted part (e.g. the control unit CONT in FIG. 6) is configured to initiate a first measurement in a first measurement time period $T_m$ (Measurement period) at a first predefined maximum time $(T_p+T_x)$ after the start of the probe pulse of said MP-stimulation signal (Masker+Probe).

The measurements of the transient of the Masker—(M) (FIG. 4a), of the Masker-Probe-(MP) (FIG. 4b), and of the nerve response and the transient of the Probe—(P) signal (FIG. 4c), are performed in a specific measurement time period (or window). The measurement time period has a duration in time denoted $T_m$ (cf. the grey rectangle denoted Measurement period in FIGS. 4a, 4b and 4c) between a measurement start time $t_{M,start}$ and a measurement end time $t_{M,end}$. Preferably, the predefined maximum time $(T_p+T_x)$ after the initiation of the P-stimulation pulse is smaller than the latency time of the auditory nerve (to ensure that the measurement time period includes the time period where a nerve response can be expected, cf. FIG. 4c). To measure the transient of the Masker and Masker-Probe pulses at the appropriate time for being used for identifying a (possible) nerve response (eCAP), the start time $t_{M,start}$ of the measurement period $T_m$ is located at the same time relative to a stimulation start time $t_{S,start}$. The start time $t_{M,start}$ of the measurement period is e.g. defined as $t_{M,start}=t_{S,start}+T_p+MPI+(T_p+T_x)$ in FIG. 4a, 4b, 4c.

Further correction steps to improve the identification of the nerve response may be added, including post-processing of the measured nerve response signal.

Figure 5:
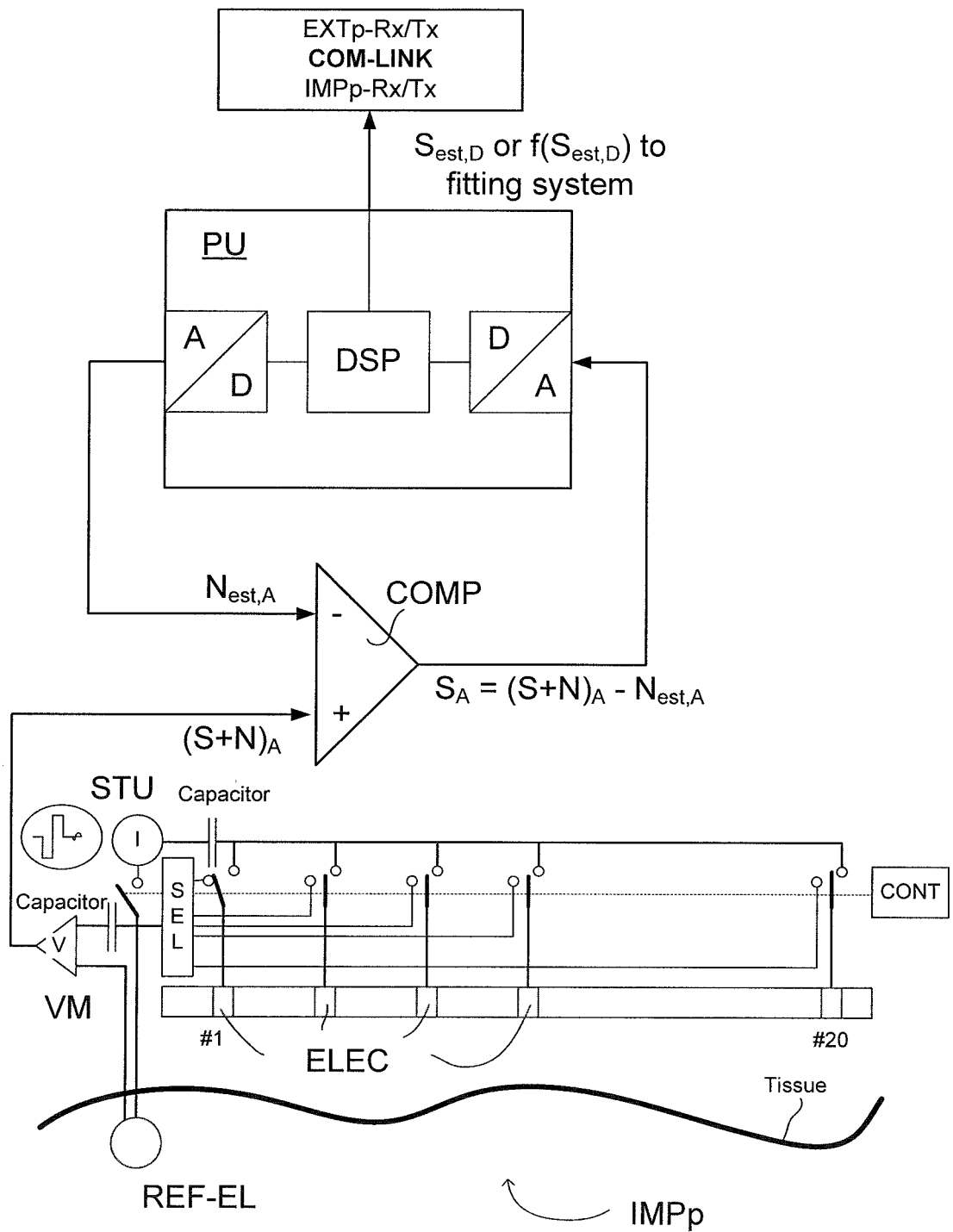

A simplified drawing of the circuitry for measuring a nerve response in an implanted part, e.g. comprising the steps indicated in FIG. 4 (e.g. only the steps of FIG. 4b, 4c) is shown in FIG. 5.

FIG. 5 shows an embodiment of a stimulation, measurement and processing part of an implanted part of a hearing assistance device according to the present disclosure.

The implanted part (IMPp) comprises a stimulation unit (STU) comprising a current source (I) for generating and applying current stimulation pulses to one or more electrodes (ELEC). The electrodes are separated from the current source (and from the measurement unit (MEU in FIG. 6), e.g. comprising voltage amplifier VM and or analogue comparator COMP) by capacitors (Capacitor, to avoid leak currents to induce electrolytic activity in the surrounding fluids). Alternatively (or additionally), the implanted part (IMPp) comprises a voltage source for generating and applying voltage pulses to one or more electrodes. Preferably, both kinds of stimulation can be applied depending on a configuration of circuitry of the implanted part, e.g. performed during fitting. Preferably, the stimulation pulses (current or voltage) is configurable (e.g. via the control unit, cf. CONT in FIG. 6) in duration $(T_p)$ and/or amplitude (cf. FIG. 4).

After a stimulation pulse has been applied to an electrode (or a pair of electrodes) and before a recording of either an artifact alone (cf. e. FIG. 4a, 4b) or an artifact and a nerve response (e.g. an eCAP, cf. FIG. 4c), the current source is disconnected from the electrodes (ELEC), cf. symbolic contact switches in FIG. 5 (and switch unit (SW) in FIG. 6). The stimulated electrode(s) or neighboring 'measurement' or recording electrode(s) is(are) then connected to a voltage measurement circuit (cf. analogue comparator COMP, e.g. an operational amplifier, e.g. a low power differential voltage amplifier, e.g. INA333 from Texas Instruments, or equivalent) instead (also via appropriate, mentioned switch elements). If one intra-cochlear electrode is used for the stimulation, the reference electrode (REF-EL) is used as 'sink' (monopolar stimulation). Alternatively, two intra-cochlear electrodes can be used for stimulation and measurement (either the same of different, bi-polar stimulation).

The selection of and application of current stimuli to particular electrodes and subsequent voltage responses are managed by a control unit (cf. unit CONT in FIG. 6), not shown in FIG. 5. A digital signal processor, the DSP, performs the artifact 'averaging' and eCAP identification.

In a fitting session, a starting value of a stimulation signal for a given stimulation electrode is e.g. based on an empirically determined medium level of stimulation intensity $I_S$. Based thereon a (possible) response signal from the auditory nerve (eCAP) with intensity $I_{ECAP}$ is identified. If a response is identified, measurements are e.g. repeated at decreasing values of stimulation intensity $I_S$. Thereby a threshold level (T) is determined, e.g. by extrapolation (or more sophisticated methods) of a measured ECAP intensity $I_{ECAP}$ vs. stimulation intensity $I_S$ curve. Comfort levels (C) are often estimated based on statistical data (High T=>high C, low T=>low C). If a response is not identified, one or more measurements at increasing values of stimulation intensity $I_S$ may be performed to determine a threshold value or to decide that the stimulation (and/or recording) electrode is not functioning. In an embodiment, the eCAP measurements are only performed for some of the electrodes (a few, e.g. 1 or 2). Alternatively, a threshold value may be determined for a majority or all electrodes. The eCAP is e.g. identified using a method as described in FIG. 4, e.g. in combination with a statistical estimator based on prior knowledge of the nerve response signal. An automated method according to the present disclosure, facilitates the measurement and computation of hearing thresholds for a multitude, such a as a majority or all of the intra-cochlear electrodes of the implanted part. Thereby the fitting of the hearing assistance device to a particular users needs becomes more accurate, and/or can be performed faster.

A measurement of a nerve response is schematically indicated in FIG. 5 and outlined in the following, where artifact signals are denoted N (Noise), nerve response signals are denoted S (Signal), an analogue signal is denoted by suffix 'A' (e.g. $N_{est,A}$, for an analogue estimated artifact signal $N_{est}$), and a digital signal is denoted by suffix 'ID' (e.g. $S_{est,D}$ for a digital estimated nerve response signal $S_{est}$):

The first input (−) to the analogue comparator (COMP) (during a nerve response measurement period) is analogue estimated time variant artifact signal $N_{est,A}$ (time variable t is not indicated). The second input (+) to the analogue comparator (COMP) is the nerve response (eCAP, S) mixed with an artifact (N). The measured signal S+N, e.g. resulting from probe stimulation pulse P, as illustrated in FIG. 4c, is analogue, and hence denoted $(S+N)_A$. The estimated artifact $N_{est,A}$ is subtracted from the nerve response plus artifact $(S+N)_A$ in the analogue comparator providing as an output analogue signal SA representing the nerve response (eCAP): $S_A=(S+N)_A−N_{est,A}$. The nerve response (eCAP) value $S_A$ is digitized in the D/A converter providing (time variant) digital nerve response value $(S_A)_D$, for further processing in the digital signal processor (DSP). The nerve response measurement may be repeated a number (Q) of times. A digital average of the eCAP may be determined as $S_{est,D} = (1/Q) \text{SUM}((S_A)_D) = \langle(S_A)_D\rangle$. Alternatively, or additionally, the processing unit (PU) is configured to estimate the nerve response from the measured (digitized) signal $((S_A)_D)$ based on a-priori knowledge of said measured signal, cf. FIG. 7 below. The identified nerve response signal (eCAP, $S_{est,D}$) or a signal $f(S_{est,D})$ derived there from may be used (e.g. in the processing unit, PU) to determine a hearing threshold for the stimulated electrode and/or be forwarded to an external part and/or to a fitting system via a communication link (COM-LINK).

$N_{est}$ is e.g. determined by repeating the Masker+Probe-stimuli shown in FIG. 4b a number of times (M) (with an appropriate idle period between each measurement) during an artifact measurement period), where the artifact $N_A(t)$ is the input to the second input (+) to the analogue comparator (COMP), the first input (−) being e.g. grounded (set to zero potential). Each artifact measurement result $N_A(t)$ digitized in the D/A converter of the processing unit (PU) and providing M digital values of $(N_A)_D(t)_i$, i=1, 2, ..., M, which are averaged in the digital signal processor (DSP), e.g. providing a digital average artifact value $\langle(N_A)_D(t)\rangle = (1/M) \text{SUM}((N_A)_D(t)_i)$. Alternatively, an averaging algorithm is used in the DSP to provide a running average, thereby avoiding the simultaneous storage of all M values). The digital average artifact value $\langle(N_A)_D(t)\rangle$ is converted to an analogue signal $N_{est,A} = (\langle(N_A)_D(t)\rangle)_A$ in the A/D converter of the processing unit (PU). Instead of calculating an average artifact as described, $N_{est}$ may be determined by other methods. In an embodiment, the artifact is estimated in an off-line procedure in advance of the use of the implant part of the hearing assistance device, e.g. by simulation. In an embodiment, the processing unit (PU) comprises a memory comprising tables of relevant artifacts (as a function of pulse amplitude), i.e. $N_{est}(t)$, $t = t_{M,start} - t_{M,end}$). A control unit having information of 1 current stimulation signals is e.g. configured to read an average artifact value $N_{est}(t)$ corresponding to the stimulation signal from the memory and subtract it from the nerve response signal in the nerve response measurement period.

Figure 6:
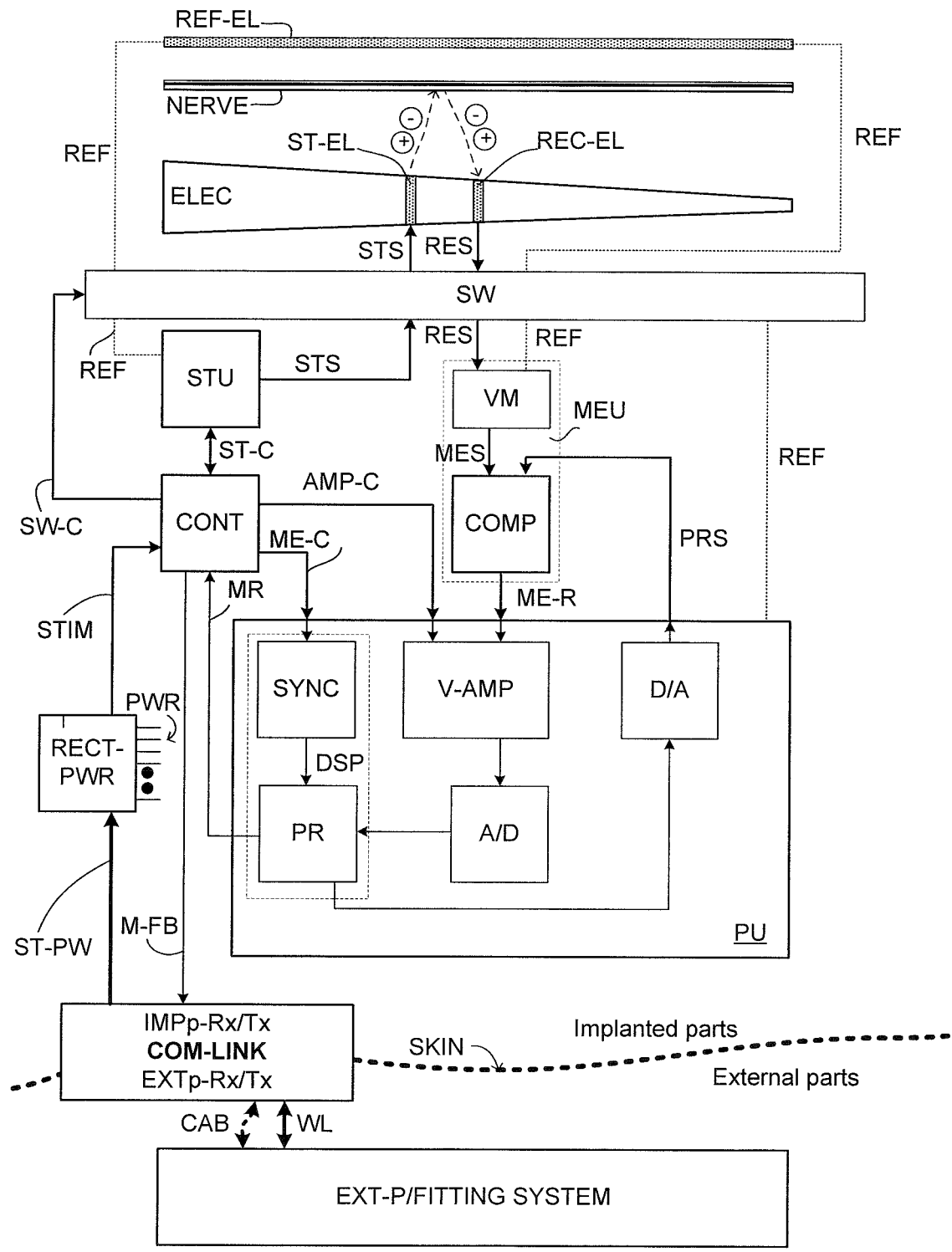

FIG. 6 shows an embodiment of an implanted part of a hearing assistance device according to the present disclosure. The embodiment of a hearing assistance device in FIG. 6 comprises the elements shown in the embodiment of an implanted part in FIG. 5 and they interact as described in connection with FIG. 5. FIG. 6 further illustrates an external part EXT-P and/or a FITTING SYSTEM which is configured to be able to exchange information with the implanted part(s) via a (wired (CAB) or wireless (WL)) communication link (COM-LINK) through the skin (SKIN) of the user. The communication link (COM-LINK) comprises transceiver units (EXTp-Rx/Tx and IMPp-Rx/Tx) in the external part(s) and in the implanted part, respectively.

The implanted part (IMPp) comprises a multitude of electrodes (ELEC) adapted for being located in the cochlea in proximity of an auditory nerve (NERVE) of the user, and a reference electrode (REF-EL) adapted for being located outside the cochlea and to provide a reference voltage (REF) to various electronic units of the implanted part. One of the electrodes is a stimulation electrode (ST-EL) and another is a recording electrode (REC-EL). The implanted part (IMPp) further comprises a stimulation unit (STU) electrically coupled to the stimulation electrode (ST-EL) during a stimulation time period and configured for applying a stimulation signal (STS) to the stimulation electrode (ST-EL). The implanted part (IMPp) further comprises a measurement unit (MEU) electrically coupled to the recording electrode (REC-EL) during a measurement time period and configured to measure a signal (RES) picked up by the recording electrode (REC-EL) in response to said stimulation signal (STS) and providing a measured signal (ME-R). The implanted part (IMPp) further comprises a control unit (CONT) configured to control the timing of the application of the stimulation signal (STS) in the stimulation time period and to control the measurement time period relative to the stimulation time period, and a processing unit (PU) configured to record the measured signal (ME-R) in the measurement time period and to identify a response (e.g. an eCAP) from the auditory nerve based on said measured signal (ME-R). The implanted part (IMPp) further comprises a switch unit (SW) comprising a number of switching elements (e.g. transistors) allowing each of said multitude of electrodes (ELEC) to be selected as a stimulation electrode (ST-EL) and/or as a recording electrode (REC-EL) at a given point in time. The control unit (CONT) is configured to control the stimulation unit (STU, via signal ST-C) and the switch unit (SW, via signal SW-C). Preferably, the processing unit (PU) is configured to generate signals or commands from the measured nerve response signals based on a criterion and to forward such signals (MR) to the control unit (CONT). Such signals or commands extracted from the measured nerve response signals (and possibly status signals of the implanted part (e.g. voltages, available energy estimates, etc.)) can e.g. be forwarded to an external part (e.g. a BTE-part) or a FITTING SYSTEM via communication link (COM-LINK), cf. signal M-FB. The measurement cycle for extracting a nerve response signal (eCAP) via the stimulation unit (STU), the electrodes (ELEC), the measurement unit (MEU, comprising voltage measurement unit VM and analogue comparator COMP), the processing unit (PU, comprising A/D and D/A converters, a variable voltage amplifier V-AMP, and a digital signal processing unit DSP) and in particular the role of analogue input signals MES and PRS to the comparator COMP is described in connection with FIGS. 4 and 5. The analogue input signal PRS from the D/A converter to the comparator (COMP) represents (in an artifact measurement mode) a constant voltage (e.g. 0 V) or (in a nerve response measurement mode) an average artifact value for being subtracted (in the analogue domain from an analogue measurement signal (MES) comprising a nerve response (eCAP). The digital signal processing unit (DSP) comprises a digital processor (PR) for processing input data (from the A/D-converter) and providing processed data a) to the D/A converter for use in the implant processing procedure and b) to the control unit (CONT) for being either forwarded to the communication interface (COM-LINK) and/or used to control the stimulation unit (STU), the voltage amplifier (V-AMP) and/or the switch unit (SVV) (and possibly the rectifier and a power supply unit (RECT-PWR)). The digital signal processing unit (DSP) comprises a synchronization unit (SYNC) (controlled by the signal ME-C from the control unit) for synchronizing the different modes of operation (stimulation and measurement of a first artifact (cf. FIG. 4a), stimulation and measurement of a second artifact (cf. FIG. 4b), stimulation and measurement of a nerve response (cf. FIG. 4b), etc.)

The implanted part further comprises a rectifier and a power supply unit (RECT-PWR) for separating stimulation signals (STIM) from power, in particular for rectifying an incoming AC-signal signal (ST-PVI) (comprising information and power) from an external part (e.g. a BTE-part) or a FITTING SYSTEM via communication link (COM-LINK). The rectifier and a power supply unit (RECT-PWR) provides the necessary supply voltages to the implanted part. In a self-contained fully implanted hearing assistance device, the rectifier and a power supply unit (RECT-PWR) is substituted by a battery, e.g. a (e.g. wirelessly) rechargeable battery.

In some prior art solutions, an averaged eCAP signal is transmitted to a fitting system and an audiologist/physician evaluates the signal and decides whether the received signal is a nerve response (eCAP) or not. Alternatively, an external system based on artificial intelligence (AI) for recognizing an eCAP has been proposed. The article by [Undurraga et al.; 2012] describes the use of statistics to decide whether or not an eCAP is present (an uncorrelated Gaussian noise distribution is assumed, eCAP=Max−Min=$P_2$−$N_1$; $P_2$ (or $P_1$)=max of positive peak of nerve response signal; $N_1$=min of negative peak of nerve response signal (the max and min values of the peaks being defined in FIG. 7).

In the present disclosure a different (statistical) method is proposed. The method is based on the Receiver Operating Characteristic (ROC) curve that graphically illustrates the performance of binary classifier (e.g. true, false) when the threshold value between 'true' and 'false' varies. This identification of eCAPs can be performed by the implanted processing unit (PU, e.g. the DSP).

In a preferred embodiment, prior knowledge on eCAP latency, amplitude and shape is systematically utilized to produce a robust estimate of patient (hearing) thresholds. An eCAP detection algorithm using a threshold criterion based on a likelihood ratio test has been designed.

In an embodiment, the nerve response identification algorithm (estimator) comprises a sampling at fixed latency algorithm using a-priori information of the nerve response. The time dependent nerve response comprising a positive peak component (P1) and a negative peak component (N1) is assumed to exhibit respective (fixed) peak latencies Lpi and Lm. In the estimator, the nerve response amplitude is taken to be $s(t=L_{P1})-s(t=L_{N1})$, where s(t) is a measured signal, and t is time.

Figure 7:
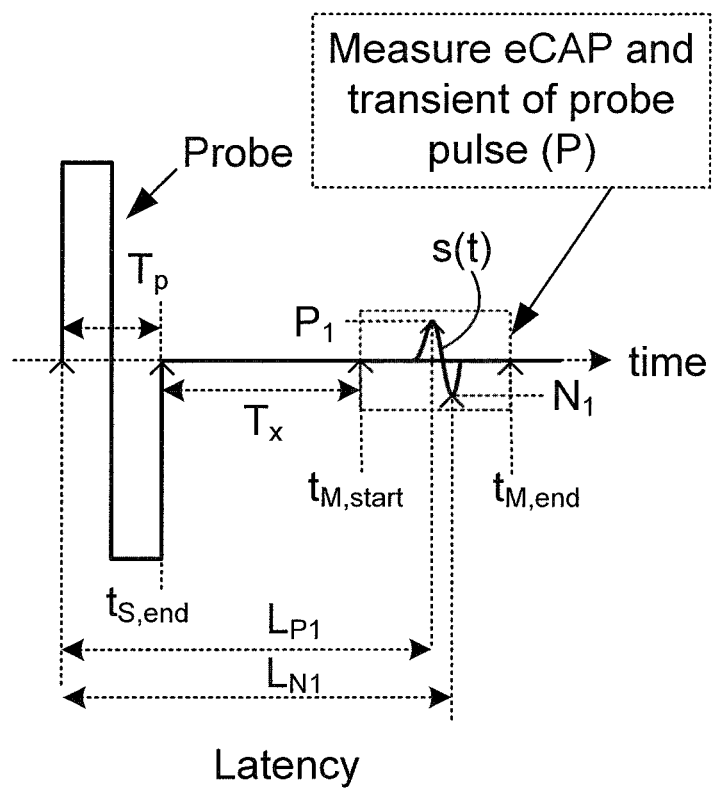

FIG. 7 schematically illustrates parameters (N1, P1, $L_{P1}$, $L_{N1}$, $s(t=L_{P1})$, and $s(t=L_{N1})$) of the fixed latency algorithm statistical estimator of a nerve response utilizing prior knowledge of peak latencies.

Preferably, however, the nerve response identification algorithm (estimator) comprises a restricted peak-picking algorithm using a-priori information of the nerve response, assumed to comprise a positive peak component ($P_1$) having positive peak latencies in the time interval between a minimum $I_{P1}$ and a maximum $L_{P1}$ latency and a negative peak component ($N_1$) having peak latencies in the interval $I_{N1}$ and $L_{N1}$, and the nerve response amplitude is taken to be MAX($s(I_{P1}<t<L_{P1})$)−MIN($s(I_{N1}<t<L_{N1})$), where s(t) is a measured signal, and t is time. This estimator for eCAP detection using a-priori knowledge on latencies to restrict peak search to the clinical range is found to provide better detection independently of the signal to noise ratio (SNR). Furthermore, it is computationally in-expensive and thus suitable for embedded real-time ECAP detection (i.e. performed by an implanted processor).

In conclusion, the implanted part comprising processing unit (PU, e.g. the DSP) can advantageously perform the following tasks:
Modeling of artifact response.
Statistical analysis of ECAP signals to identify true nerve response signals.
Determined hearing thresholds
Perform other electrically (or acoustically) evoked potential measurements (e.g. Brainstem measurements)

The latter is performed by changing the sampling frequency of the A/D converter, the implanted system can measure Auditory Brainstem Responses (ABR) and other (weak) signals originating from the brain farther away from the auditory nerves of cochlea (responsible for the ECAPs).

The invention is defined by the features of the independent claim(s). Preferred embodiments are defined in the dependent claims. Any reference numerals in the claims are intended to be non-limiting for their scope.

Some preferred embodiments have been shown in the foregoing, but it should be stressed that the invention is not limited to these, but may be embodied in other ways within the subject-matter defined in the following claims and equivalents thereof.

REFERENCES

[Schaub; 2008] Arthur Schaub, Digital hearing Aids, Thieme Medical. Pub., 2008.
[Clark; 2003] Graeme Clark, Cochlear Implants, Fundamentals and Applications, AIP Press, Springer Science+Business Media, Inc., New York, N.Y., 2003.
[Brown et al.; 1990] Carolyn J. Brown, Paul J. Abbas, and Bruce Gantz, Electrically evoked whole-nerve action potentials: Data from human cochlear implant users, J. Acoust. Soc. Am., Volume 88, Issue 3, pp. 1385-1391 (1990).
[de Sauvage et al.; 1983] Renaud Charlet de Sauvage, Yves Cazals, Jean-Paul Erre, and Jean-Marie Aran, Acoustically derived auditory nerve action potential evoked by electrical stimulation: An estimation of the waveform of single unit contribution, J. Acoust. Soc. Am., Volume 73, Issue 2, pp. 616-627 (1983).
[Undurraga et al.; 2012] Jaime A. Undurraga, Robert P. Carlyon, Jan Wouters, and Astrid van Wieringen, Evaluating the Noise in Electrically Evoked Compound Action Potential Measurements in Cochlear Implants, IEEE Transactions on Biomedical Engineering, Vol. 59, No 7, July 2012, pp. 1912-1923.

The invention claimed is:

1. A hearing assistance device comprising an implanted part adapted for being implanted at a user's ear, wherein the implanted part comprises
A multitude of electrodes adapted for being located in the cochlea in proximity of an auditory nerve of the user;
Stimulation circuitry electrically coupled to a stimulation electrode during a stimulation time period and configured for applying a stimulation signal to the stimulation electrode;
Measurement circuitry electrically coupled to a recording electrode during a measurement time period and configured to measure a signal picked up by the recording electrode in response to said stimulation signal and providing a measured signal;
A control unit configured to control the timing of the application of the stimulation signal in the stimulation time period and to control the measurement time period relative to the stimulation time period;

A processing unit configured to record the measured signal in the measurement time period and to identify a response from the auditory nerve based on said measured signal, wherein the measurement circuitry comprises an analogue comparator comprising first and second inputs and an output representing a comparison of the first and second inputs, wherein the first input is operationally coupled to said recording electrode to receive the measured signal during said measurement time period, controlled by the control unit, and said second input is configured to receive an estimated time variant artifact signal, the processing unit comprises a digital processor and an AD-DA-interface to said analogue comparator, the AD-DA-interface having an analogue input and an analogue output, an analogue output of the AD-DA-interface is operationally coupled to the second input of the analogue comparator, and the processing unit supplies the estimated time variant artifact signal to the second input via the AD-DA interface, and the output of the analogue comparator, which provides a result of subtracting the estimated time variant artifact signal from the measured signal, is operationally coupled to an analogue input of the AD-DA-interface of the processing unit.

2. A hearing assistance device according to claim 1 wherein the processing unit is configured to compute at least one estimator of at least one statistical variable obtained from said measured signal.

3. A hearing assistance device according to claim 2 configured to use said at least one statistical estimator to identify said response from the auditory nerve.

4. A hearing assistance device according to claim 2 configured to generate signals or commands based on a criterion applied to said at least one estimator computed in the processing unit.

5. A hearing assistance device according to claim 1 comprising a switch unit comprising a number of switching elements allowing each of said multitude of electrodes to be selected as a stimulation electrode and/or as a recording electrode at a given point in time.

6. A hearing assistance device according to claim 5 wherein the control unit is configured to use said signals or commands to control the stimulation unit and the switch unit.

7. A hearing assistance device according to claim 1 wherein the control unit is configured to identify said response from the auditory nerve for a given stimulation electrode for a number of different levels of the stimulation signal, and to determine a threshold level of stimulation from said responses from the auditory nerve.

8. A hearing assistance device according to claim 1 wherein the AD-DA interface comprises a variable amplifier for amplifying an input to the AD-DA interface by a configurable amplification factor.

9. A hearing assistance device according to claim 1 wherein the control unit is configured to change a sampling rate and/or an amplification factor of the AD-DA interface, whereby signals from other parts of the nerve system between cochlea and the hearing centre of the brain can be extracted.

10. A method of operating a hearing assistance device comprising an implanted part adapted for being implanted at a user's ear, the implanted part comprising a multitude of electrodes adapted for being located in the cochlea in proximity of an auditory nerve of the user, wherein the method comprises electrically coupling stimulation circuitry to a stimulation electrode during a stimulation time period and applying a stimulation signal to the stimulation electrode;

electrically coupling measurement circuitry to a recording electrode during a measurement time period and measuring a signal picked up by the recording electrode in response to said stimulation signal and providing a measured signal;

controlling the timing of the application of the stimulation signal in the stimulation time period and the measurement time period relative to the stimulation time period;

identifying, by a processing unit, a response from the auditory nerve based on said measured signal, the processing unit comprising an AD-DA-interface, wherein the recording electrode is operationally coupled to an analogue comparator, the recording electrode providing the measured signal during said measurement time period to a first input of the analogue comparator, and wherein the method further comprises supplying, from the processing unit, an estimated time variant artifact signal to a second input of the analogue comparator via the AD-DA interface; and outputting from the analogue comparator a result of subtracting the estimated time variant artifact signal from the measured signal to the processing unit via the AD-DA interface.

11. A method according to claim 10 comprising the step of modifying the electrical stimulation depending on whether a response from the auditory nerve was identified or not.

12. A method according to claim 10 wherein the step of identifying a response from the auditory nerve based on said measured signal comprises an averaging procedure wherein a number of measured signals from the recording electrode is averaged.

13. A method according to claim 10 wherein the step of identifying a response from the auditory nerve based on the measured signal comprises a statistical identification algorithm for identifying a nerve response based on priori knowledge of the measured signal.

14. A method according to claim 13 wherein the nerve response identification algorithm comprises a restricted peak-picking algorithm using a-priori information of the nerve response, assumed to comprise a positive peak component ($P_1$) having positive peak latencies in a time interval between a first minimum latency ($l_{P1}$) and a first maximum latency ($L_{P1}$) latency and a negative peak component ($N_1$) having peak latencies in a time interval between a second minimum latency ($l_{N1}$) and a second maximum latency ($L_{N1}$), and a nerve response amplitude is taken to be MAX($s(l_{P1}<t<L_{P1})$)−MIN($s(l_{N1}<t<L_{N1})$), where s(t) is the measured signal, and t is time.

* * * * *